(12) United States Patent
Klee et al.

(10) Patent No.: US 11,351,418 B2
(45) Date of Patent: Jun. 7, 2022

(54) BREATHING TRAINING, MONITORING AND/OR ASSISTANCE DEVICE

(71) Applicant: KONINKLIJKE PHILIPS N.V., Eindhoven (NL)

(72) Inventors: Mareike Klee, Straelen (DE); Franciscus Hendrikus Van Heesch, Eindhoven (NL); Manuela Lunz, Waalre (NL); Neil Francis Joye, Waalre (NL); Lenneke Van Genugten, Eindhoven (NL); Kevin Paul Warmerdam, Eindhoven (NL); Edwin Van Rutten, Eindhoven (NL); Privender Kaur Saini, Eindhoven (NL); Gabriele Spina, Eindhoven (NL); Albertus Cornelis Den Brinker, Eindhoven (NL); Sander Kruitwagen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 278 days.

(21) Appl. No.: 15/771,101

(22) PCT Filed: Oct. 21, 2016

(86) PCT No.: PCT/EP2016/075331
§ 371 (c)(1),
(2) Date: Apr. 27, 2018

(87) PCT Pub. No.: WO2017/072036
PCT Pub. Date: May 4, 2017

(65) Prior Publication Data
US 2018/0318643 A1    Nov. 8, 2018

(30) Foreign Application Priority Data
Oct. 30, 2015  (EP) .................................... 15192420

(51) Int. Cl.
*A63B 23/18*    (2006.01)
*A63B 24/00*    (2006.01)
(Continued)

(52) U.S. Cl.
CPC ............ *A63B 23/185* (2013.01); *A61B 5/097* (2013.01); *A61B 5/6898* (2013.01);
(Continued)

(58) Field of Classification Search
CPC ............ A63B 71/0622; A63B 24/0087; A63B 21/0087; A63B 21/00069;
(Continued)

(56) References Cited

U.S. PATENT DOCUMENTS 8,161,966 B2    4/2012  Foley
8,758,202 B2    6/2014  Foley
(Continued)

FOREIGN PATENT DOCUMENTS

CN    102726256 A    10/2012
CN    103736256 A    4/2014
(Continued)

OTHER PUBLICATIONS

Abushakra, A. et al., "Augumenting Breath Regulation Using a Mobile Driven Virtual Reality Therapy Framework", Biomedical and Health Informatics, vol. 18 , Issue 3, 2013, pp. 746-752 **U.S. Government work not protected by U.S. copyright—This article has been accepted for publication in a future issue of this journal, but has not been fully edited. Content may change prior to final publication.
(Continued)

*Primary Examiner* — Joseph D. Boecker
*Assistant Examiner* — Brian T Khong
(74) *Attorney, Agent, or Firm* — Daniel H. Brean

(57) ABSTRACT

A breathing training, monitoring and/or assistance device is provided for home use. The device is for providing support
(Continued)

and guidance during the training of breathing exercises. The device takes account of external data which relates to one or more of: the environmental conditions in which the device is being used; activity information in respect of the user; physiological sensor data about the user which is not related to breathing characteristics.

16 Claims, 6 Drawing Sheets

(51) Int. Cl.
- A61B 5/097 (2006.01)
- A61B 5/00 (2006.01)
- A61B 5/08 (2006.01)
- A61B 5/087 (2006.01)
- A61B 5/085 (2006.01)
- A61B 5/091 (2006.01)
- A63B 71/06 (2006.01)
- A63B 21/00 (2006.01)
- A61M 16/00 (2006.01)

(52) U.S. Cl.
CPC ..... *A61M 16/026* (2017.08); *A63B 21/00069* (2013.01); *A63B 24/0087* (2013.01); *A63B 71/0622* (2013.01); *A61B 5/085* (2013.01); *A61B 5/087* (2013.01); *A61B 5/0816* (2013.01); *A61B 5/091* (2013.01); *A61B 5/486* (2013.01); *A61B 2505/09* (2013.01); *A61B 2560/0242* (2013.01); *A61M 2016/003* (2013.01); *A61M 2016/0027* (2013.01); *A61M 2205/50* (2013.01); *A61M 2205/502* (2013.01); *A61M 2205/582* (2013.01); *A61M 2205/583* (2013.01); *A61M 2205/8206* (2013.01); *A63B 2024/0093* (2013.01); *A63B 2024/0096* (2013.01); *A63B 2071/0625* (2013.01); *A63B 2071/0655* (2013.01); *A63B 2213/005* (2013.01); *A63B 2220/00* (2013.01); *A63B 2220/12* (2013.01); *A63B 2220/40* (2013.01); *A63B 2220/56* (2013.01); *A63B 2220/808* (2013.01); *A63B 2220/836* (2013.01); *A63B 2225/20* (2013.01); *A63B 2225/50* (2013.01); *A63B 2225/74* (2020.08); *A63B 2230/06* (2013.01); *A63B 2230/207* (2013.01); *A63B 2230/30* (2013.01); *A63B 2230/40* (2013.01); *A63B 2230/42* (2013.01)

(58) Field of Classification Search
CPC ........ A63B 2024/0093; A63B 24/0069; A61B 5/08; A61B 5/087; A61B 5/0871; A61B 5/0873; A61B 5/087509; A61B 5/091; A61B 5/093; A61B 5/0875; A61B 5/09
See application file for complete search history.

(56) References Cited

U.S. PATENT DOCUMENTS

| | | | |
|---|---|---|---|
| 8,807,131 | B1 | 8/2014 | Tunnell |
| 2002/0096174 | A1 | 7/2002 | Hill |
| 2005/0111365 | A1 | 5/2005 | Stark |
| 2007/0219059 | A1 | 9/2007 | Schwartz |
| 2009/0170664 | A1 | 7/2009 | Kario |
| 2010/0240945 | A1* | 9/2010 | Bikko ................ A61B 5/02405 600/28 |
| 2011/0105279 | A1 | 5/2011 | Herranen |
| 2012/0085347 | A1* | 4/2012 | Iyer ................... A61M 16/0666 128/204.21 |
| 2012/0209533 | A1 | 8/2012 | Kodama |
| 2012/0240945 | A1 | 9/2012 | Laplante et al. |
| 2013/0116807 | A1 | 5/2013 | Cheung |
| 2013/0310636 | A1* | 11/2013 | Krans ...................... A61B 5/08 600/26 |
| 2014/0044372 | A1 | 2/2014 | Mertens |
| 2014/0121540 | A1 | 5/2014 | Raskin |
| 2014/0352690 | A1* | 12/2014 | Kolb ................. A61M 15/0085 128/200.16 |
| 2015/0111612 | A1 | 4/2015 | Armstrong |
| 2015/0186609 | A1 | 7/2015 | Utter, II |
| 2015/0196804 | A1 | 7/2015 | Koduri |
| 2015/0250385 | A1 | 9/2015 | Ahmed |
| 2015/0258370 | A1* | 9/2015 | Arkush .................. A61B 5/486 482/8 |
| 2015/0320955 | A1 | 11/2015 | Mahadevan |
| 2016/0179103 | A1* | 6/2016 | Paradis ................... F01D 17/10 137/78.1 |
| 2016/0325058 | A1* | 11/2016 | Samson ................. A61B 5/087 |
| 2018/0318643 | A1 | 11/2018 | Den Brinker |

FOREIGN PATENT DOCUMENTS

| | | | | |
|---|---|---|---|---|
| WO | WO2006042415 | A1 | 4/2006 | |
| WO | WO2010015865 | A1 | 2/2010 | |
| WO | WO20121173776 | A1 | 9/2012 | |
| WO | WO-2013179173 | A1 * | 12/2013 | .......... A61M 15/009 |
| WO | WO2014004437 | A1 | 1/2014 | |
| WO | WO2014068504 | A2 | 5/2014 | |

OTHER PUBLICATIONS

Abushakra, A. et al., "An Automated Approach Towards Estimating Lung Capacity from Respiration Sounds", IEEE Healthcare Innovations Conference (HIC'12), ResearchGate, Jan. 2012.

* cited by examiner

BREATHING TRAINING, MONITORING AND/OR ASSISTANCE DEVICE

CROSS-REFERENCE TO RELATED APPLICATIONS

This patent application claims the priority benefit under 35 U.S.C. § 371 of international patent application no. PCT/EP2016/075331, filed Oct. 21, 2016, which claims the benefit of European Application No. EP15192426.3, filed Oct. 30, 2015, which claims the benefit of European Application No. EP15192429.6, filed Oct. 30, 2015, and which claims the benefit of European Application No. EP16153113.2, filed Jan. 28, 2016. These applications are hereby incorporated by reference herein.

FIELD OF THE INVENTION

This invention relates to apparatus and methods relating to monitoring or assisting breathing in patients.

BACKGROUND OF THE INVENTION

Over 1 Billion people suffer from respiratory diseases such as chronic obstructive pulmonary diseases, asthma, cystic fibrosis or neuromuscular disorders that affect patients' muscles and reduce lung function.

Chronic obstructive pulmonary disease (COPD) refers broadly to a group of conditions that cause irreversible respiratory impairment by increasing obstruction to airflow through the bronchi of the lungs. COPD typically has two components which may be present to varying degrees. The first is chronic obstructive bronchitis where the airways become reduced in volume, showing increased airway resistance making it more difficult to move air out of the lung. The second is pulmonary emphysema, where the small air sacs are ruptured causing air to be retained in the lungs and limit the available space during inhalation.

Individuals who predominantly have emphysema experience symptoms that differ in detail from those who predominantly have chronic bronchitis; however, both disorders contribute to shortness of breath during exercise and to general disability.

200 Million people worldwide suffer from COPD and it is predicted to become the third leading cause of death and disease worldwide by 2020, mainly due to its growing prevalence in developing and low income countries.

Chronic obstructive pulmonary disease is progressive and irreversible. It is an under-diagnosed, life-threatening lung disease that interferes with normal breathing. The primary cause of COPD is tobacco smoke. Other risk factors for COPD are indoor and outdoor air pollution, occupational dusts and chemicals.

The most common symptoms of patients with COPD are breathlessness, abnormal sputum with respect to volume and color, and chronic coughing. Breathlessness, or dyspnea, is the number one complaint by diagnosed or non-diagnosed COPD patients. Daily activities, such as walking up stairs can become very difficult due to breathlessness as the condition gradually worsens. Furthermore cough and getting rid of secretions that build up in the lungs is an issue for patients with COPD. COPD patients can be very prone to lung infections and pneumonia, which can cause a downward spiral of repeated lung infections and a further decline of lung function.

If symptoms are increasing, e.g. breathlessness or coughing, patients become anxious that their condition is deteriorating, especially patients living alone. Anxiety affects their quality of life as well as their health situation and contributes to worsening of their conditions, since with increasing anxiety patients become less active due to fear, e.g. to go outside alone or due to fear that they may run out of oxygen. With lower activity the condition of the patients worsens and the risk for hospitalization increases.

Acute exacerbations of COPD patients have a negative impact on their health related quality of life, pulmonary function and survival of patients with COPD. When COPD patients have an acute exacerbation, they are in most cases admitted to the hospital. They receive interventions such as non-invasive ventilation (NIV), medication treatment, and/or oxygen treatment to improve their conditions. At discharge, even if respiratory functions of the patients have been improved, most patients are nervous and anxious to be discharged to their home. Patients report that they do not feel better although the clinical judgment indicates this. Anxiety of being alone at home with the disease affecting patients them and does not support their recovery phase.

There is currently no cure for COPD patients and very few effective homecare solutions are available to alleviate symptoms.

There are a number of additional ways to assist such patients, and various such measures are described in this application.

It has been recognized that performing physical and breathing exercises can help to stabilize COPD symptoms and allow patients to get in control of their symptoms as part of disease self-management, also reducing the experience of anxiety.

This is addressed in pulmonary rehabilitation programs that are however only available to a limited number of patients due to the highly limited number of centers providing these programs as well as the associated cost and time off work. Furthermore, as they only last for a short time, the transfer of these exercises to the home situation and starting new, healthy habits might not be very efficient. Most patients quickly fall back into their normal and in most cases more passive lifestyle, which promotes a faster disease progression and deterioration. Consequently, even though applying simple breathing techniques could help them recover more quickly from shortness of breath, COPD patients will most likely not apply them.

By way of example, one breathing exercise is a pursed lip breathing exercise. The exercise begins by breathing in through the nose for about 2 seconds. Then the lips are puckered as if to get ready to blow out candles on a birthday cake. Breathing out slowly through pursed lips should take two to three times as long as breathing in. This exercise is typically repeated several times.

The pursed lip breathing technique slows down the breathing rate and keeps airways open longer so lungs can get rid of more stale, trapped air. It reduces the work of breathing, increases the amount of time patients can exercise or perform an activity and improves the exchange of oxygen and carbon dioxide. Normally, a patient can attain an exhalation (over) pressure level of 4 cm $H_2O$ (=382 Pa), whereas ideally, it should be 8 cm $H_2O$ (=785 Pa). The latter pressure level can be provided by a Positive Expiratory End Pressure (PEEP) or a Bilevel Positive Airway Pressure (BiPAP) device.

Another breathing exercise is a diaphragmatic breathing exercise. This is a more demanding exercise than pursed lip breathing and it is important that, before starting, the patient is relaxed and in a good position/posture to perform the exercise. Therefore it is important to take time to prepare before starting the exercise. To perform the exercise the patient is asked to place one hand just above the belt line, and the other on the chest, right over the breastbone to monitor the movement of belly and chest.

All the work should be done by the belly and the chest and shoulders should be more or less still. The next step is to open the mouth and gently sigh, as if someone had just told you something really annoying. This is to let go of all the air. During this exhaling step the shoulders and the muscles of the upper body should be relaxed, and fall down. Then the patient should close the mouth and pause for a few seconds. In the next step the patient is asked to keep the mouth closed and inhale slowly through the nose by relaxing the abdominal muscles and pushing their belly out. In the same time the waist and parts of the back can feel like expanding.

The movement of the belly precedes the inhalation by just the tiniest fraction of a second, because it is this motion (relaxation of the diaphragm) which is pulling the air in. When having inhaled as much air as is comfortable, without raising chest or shoulders, the patient is asked to stop and is finished with the inhaling. These actions can be monitored by tracking the motion of the belly and possibly the shoulders/chest by hand or via other means. After pausing briefly for whatever time feels comfortable, the patient is asked to repeat the exercise by opening the mouth and exhaling through the mouth by pushing in/contracting the belly and inhaling slowly as described above.

Training in breathing exercises such as those outlined above assists in breaking through the "vicious cycle" of disease progression through lack of exercise. During pulmonary rehabilitation, patients are educated about the disease and are trained on the breathing exercises as well as to be physically active. However, some patients do not have the possibility (availability, cost . . . ) to join such a program while others are not able to translate the learning into long term habits.

US 2014/0178844 discloses a breathing training system which can be used in the home, and thus attempts to address some of the problems outlined above.

The biggest problem of training breathing exercises is the adherence as the exercises have to become part of a daily routine to prove effective. Furthermore, the assistance of breathing exercises should be available in acute moments.

A training system should therefore have ease of use, have interactivity so that it is fun or engaging, give clear guidance but without drawing the attention of third parties, be personalized and optimized to suit the individual patient needs, and should give relevant feedback to the patient (together with their caregivers).

For COPD patients-and to a certain extend also for Asthma patients—breathing performance is indicative of the severity of the condition. The breathing performance is typically determined in a clinical practice by determining some of the following respiratory parameters:
1. Minute ventilation (VE)
2. Respiration frequency ($f_R$)
3. Breath by breath respiratory time ($T_{TOT}$)
4. Inspiratory time ($T_I$)
5. Expiratory time ($T_E$)
6. Inspiration to expiration time ratio ($T_I/T_E$)
7. Fractional inspiration time ($T_I/T_{TOT}$)
8. Cough
9. Flow estimation For example, a high $f_R$, low $T_I/T_{TOT}$ or low $T_I/T_E$ may indicate obstruction of a subject's airways.

Moreover, the delay of normal emptying of the lungs during expiration due to flow limitation, which is aggravated during exercise, leads to dynamic hyperinflation related to the increase in the respiratory frequency ($f_R$). This results in increased work of breathing, increased load on the respiratory muscles, and the intensified perception of respiratory discomfort.

It would be beneficial if at least some of these parameters could be recorded by a breathing training system to provide information of clinical relevance to the patient or to the patient's caregiver.

Apart from breathing training, another way to provide assistance to a patient is to deliver oxygen to the patient. When a patient experiences shortness of breath and needs such assistance (despite breathing training), there are various devices designed to provide such assistance.

Two main devices are used to combat shortness of breath in COPD (and other) patients.

A first is a Positive Expiratory Pressure (PEP) device, which produces the effect of a positive counter pressure upon exhaling by blowing through a restriction. For example a pursed lip breathing device is disclosed in WO 2004/096110. The pressure-flow rate relation of a restriction is super-linear, meaning that the pressure drops more than the flow rate does, tending towards lower values at the end of exhalation. While PEP may train the muscles, it does not prevent the closure of the lungs before complete emptying.

For optimal treatment of shortness of breath, a Positive Expiratory End Pressure (PEEP) is needed in combination with a long enough exhalation time.

It has also been suggested that inhalation through a restriction, to create an under-pressure upon inhaling, is also beneficial. This may for example apply when exercising with such a device. As mentioned above, pursed lip breathing is a known technique the patient can perform him/herself, but is limited to producing for example only 4 cm $H_2O$ pressure (=382 Pa), whereas for example 8 cm $H_2O$ is more optimal (=785 Pa). Of course, the desired pressure levels to be attained by the subject will depend on the nature of the subject, such as their age and their respiratory condition. These devices are cheap and may be paid out-of-pocket by the patients themselves.

An alternative approach developed by the applicant is a system (called "VitaBreath" (trade mark)) by which a patient blows against a blower upon exhalation, maintaining 8 cm $H_2O$ counter-pressure (=785 Pa) and upon inhalation delivers a positive pressure of 18 cm $H_2O$ (=1770 Pa). Details may be found in WO 2013/179173. The blower switches between the two pressure levels by rapidly changing a rotation rate. This device can often only be acquired with reimbursement from health insurance.

COPD patients may suffer from both too high carbon dioxide levels and too low oxygen levels. The delivery of oxygen is known but only severe patients receive medical treatment with additional enriched oxygen flow rates starting from 1 liter per second, requiring very advanced equipment.

Thus, although it is known that positive pressure support and oxygen can help to reduce the symptoms of COPD and other conditions, there is no small, lightweight, portable device available that can be used intermittently or only when needed, to rapidly reduce the shortness of breath during a normal daily activity such as vacuum cleaning, climbing the stairs etc.

It can be seen from the discussion above, that there remain several issues with existing systems for providing breathing training, monitoring and/or assistance. This invention relates to devices and method which provide solutions for at least some of these problems.

SUMMARY OF THE INVENTION

The invention is defined by the claims.

Examples in accordance with an aspect of the invention provide a portable breathing assistance or training device, comprising:
  a housing which defines a mouthpiece;
  a sensor arrangement for sensing breathing characteristics of a user;
  an input for receiving external data, wherein the external data relates to one or more of:
    the environmental conditions in which the device is being used;
    activity information in respect of the user;
    physiological sensor data about the user which is not related to breathing characteristics; and
    an identification of other medical assistance devices being used by the user; and
  an output indicator adapted to provide output information relating to breathing instructions or exercises and taking into account the sensed breathing characteristics and the external data, thereby to tailor a breathing exercise or training program, wherein the tailoring relates to the time at which exercises or training is to take place and/or the nature of exercises and targets to be set for the user.

By taking account of external data, the device is able to tailor the exercise or training program to the current or predicted conditions. The tailoring may relate to the time at which exercises or training is to take place, or the timing at which breathing assistance is to be provided, or the nature of exercises and targets to be set for the user.

The environmental conditions may comprise one or more of:
  the temperature;
  the time of day;
  the weather conditions;
  the air humidity;
  the air quality e.g. ozone information or air quality warnings;
  the location;
  the noise levels; and
  the speed of movement.

These may all impact on the breathing performance that can be expected from a user and/or the ability to perform exercises. The location may for example be used to discriminate between a home and a workplace, and the noise levels may be used to give an indication of the number of other people in the vicinity. The availability of sports equipment for example depends on the location. The moment of the exercise or the type of exercise might for example be adjusted depending on the nature of the space the person is in. The location information could be obtained using GPS or simply using the agenda of the subject. Speed of movement information may also be obtained by a GPS system for example to determine that the subject is in a transportation system.

The activity information may comprise one or more of:
  a current activity level of the user;
  a past activity level of the user; and
  a future activity schedule of the user.

In this way, timing of assistance or an exercise may be selected to fit within a pattern of present, past or predicted activity levels of the user.

The physiological sensor data may represent one or more of:
  sleep quality information;
  a blood oxygen saturation level;
  a heart rate;
  a stress or anxiety level.

These physiological indicators may also all impact on the breathing performance that can be expected from a user.

The sensor arrangement for sensing breathing characteristics of a user may be for measuring the breathing volume and/or the breathing amplitude and/or the breathing frequency or pattern.

A controller may be provided for controlling the timing at which an output indication is provided, based on a prediction of when an output is most suitable, taking into account the external data.

Note that the term "assistance" is used to indicate that an output may be provided to the user to guide them in their breathing. In some optional examples, the assistance may extend to providing a source of gas (i.e. oxygen) for the user for emergency occasions.

The output information is for example to indicate adherence to breathing exercises, or to provide breathing training, or to indicate correct breathing performance, or to provide advisory timing information. In one example the output information is for instructing the user to breathe at a certain rate, for example to inhale for a particular time period and to exhale for a particular time period. An instruction to exhale for a particular time period will take into account a reference breathing pattern for the user and the sensed breathing characteristics. The instructions then evolve over time to reflect the performance of the user.

The device may further comprise a connector for receiving a portable source of pressurized gas, for providing gas to the user at a pressure above atmospheric pressure. In this way, the device also provides a supply of gas (e.g. air or air with enriched oxygen). The device then functions both as a training aid and an emergency device.

The device may further comprise a portable gas canister.

A system may comprise the portable breathing assistance or training device as defined above and a portable display device for providing breathing exercise or training instructions to a user.

The invention also provides a method of providing breathing assistance or training, comprising:
  providing instructions for breathing exercises or training to a user;
  sensing breathing characteristics of the user during the exercises or training;
  receiving external data, wherein the external data relates to one or more of:
    the environmental conditions in which the device is being used;
    activity information in respect of the user;
    physiological sensor data about the user which is not related to breathing characteristics; and
    a indicator of other medical assistance devices being used by the user; and
  providing output information relating to breathing instructions or exercises or to breathing performance and taking into account the sensed breathing characteristics and the external data.

The method may comprise controlling the timing at which an output indication is provided, based on a prediction of when an output is most suitable, taking into account the external data.

A communication system may be provided for transmitting the sensor arrangement signals to a remote (display) device for setting and/or monitoring adherence to the breathing exercises or training. This provides a convenient system for the user. The communication may be over a wireless connection.

When a gas canister is used, it may have a volume of between 0.2 and 1.0 L, for example between 0.2 L and 0.6 L. By mixing with ambient air, a small volume canister may be used to provide support for a reasonable length of time. This enables a small portable device to be created. The pressure of the canister is for example between 10 atm (1013250 Pa) and 20 atm (2026500 Pa).

BRIEF DESCRIPTION OF THE DRAWINGS

Examples of the invention will now be described in detail with reference to the accompanying drawings, in which.

DETAILED DESCRIPTION OF THE EMBODIMENTS

The invention provides various improvements to breathing training, monitoring and/or assistance devices. It relates to breathing training, and provides a system for home use, which is designed as a modular system for providing guidance, motivation and confidence to apply breathing techniques advised to COPD (or other) patients. The system is for providing support and guidance during the training of breathing exercises.

The device takes account of external data which relates to one or more of:
the environmental conditions in which the device is being used;
activity information in respect of the user;
physiological sensor data about the user which is not related to breathing characteristics.

In addition, in some implementations it acts as an intervention tool in acute moments of shortness of breath, e.g. after physical activity. By then helping the patients to regain their normal or optimal breathing rhythm more quickly, it helps them to stay more active. The system can be extended and adjusted according to the patient's need to serve them optimally during the different phases of the disease.

Figure 1:
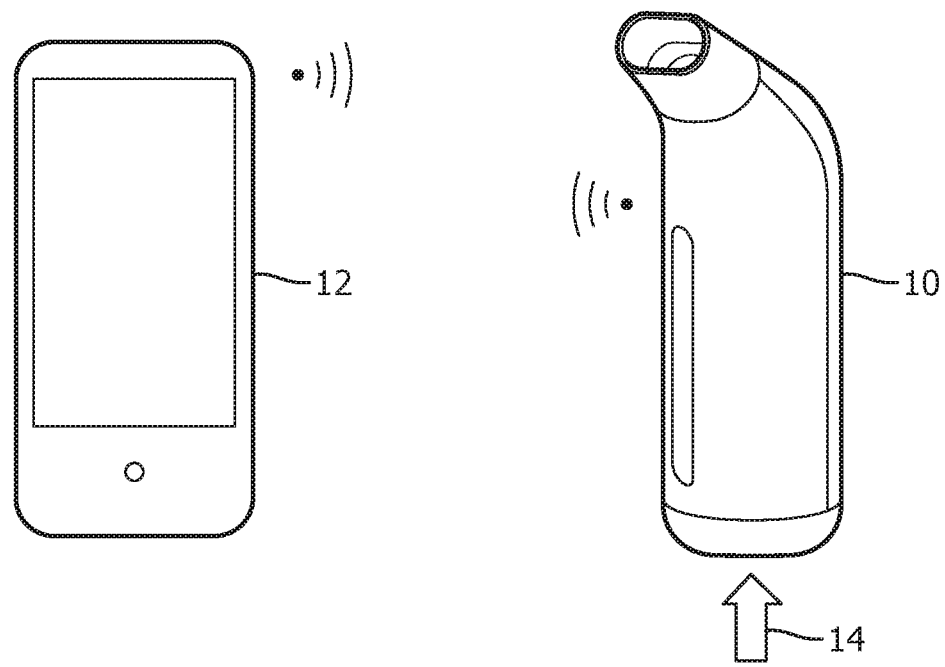
FIG. 1 shows a portable breathing assistance or training device.

The system is shown in FIG. 1. It comprises a portable breathing assist device 10 used to support COPD patients in the exercise and application of breathing techniques, and a remote display device 12 which provides a user interface.

The display device 12 is shown as a smart phone on which an app is loaded so that the display device 12 communicates wirelessly with the breathing assist device 10. The display device may connect to a remote platform hosting services to provide extended functionality and services.

The device has internal sensors 12 for sensing a first set of parameters and it also receives as input external data 14 either from the remote device 12 or directly from external sources, for example wirelessly over the internet.

The breathing assist device comprises a housing which defines a mouthpiece as shown. Within the housing is a sensor arrangement for sensing breathing characteristics of the user.

In a most basic implementation, a device is used to measure breathing rate of the user, and provide feedback to the user, while additionally providing pressure feedback so that the system provides a positive expiratory end pressure.

In more advanced implementations, a gas canister is housed in the base of the housing, for providing gas to the user at a pressure above atmospheric pressure, for assisting the user during acute events.

The pressure feedback system may then also provide pressure control during gas delivery which takes place during an inhalation cycle.

The user interface can be realized in different ways. The display device 12 may be used on its own to practice breathing exercises, with options for up-grades. The breathing assist device 10 may also be used on its own used to give feedback about breathing exercises, to support breathing, and also provide positive pressure support during exhalation (PEEP).

The two devices may be used together to offer more options, for example exercises which take the form of games or other entertaining or engaging ways to encourage the correct performance of the exercises. The overall system can also provide more precise data collection, for example measuring flow as well as breathing events. The app on the display device can act as a data collector and connection to a remote platform, although this can be integrated in the breathing assist device 10.

The system is designed to deliver an optimized training and intervention experience. By collecting data on the execution, performance and frequency of use a patient history can be established that helps to monitor the status and progression of COPD.

To provide active breathing training, the system is preferably adapted to measure breathing related parameters, such as breathing rate/breathing pattern, flow, overall exhaled volume, attained pressure, etc., and to determine irregularities and fluctuations in these parameters.

The device can operate in different modes.

In a training mode, an indication can be provided of the time during which the patient should be exhaling and/or the pressure that should be reached, and an indication of whether these targets are met. The user interface for example also provides guidance and support for applying pursed lip breathing. In general, the system can measure the performance and effectiveness of the breathing exercises and provide appropriate coaching.

In a mode where the system is used to overcome a shortness of breath e.g. induced by physical activity, the system can provide an evaluation of the initial breathing rate range (e.g. red for very fast breathing). The scale may depend on previous usage, so that the system is implemented as a self-learning system.

The indication for the time of exhalation may be slowly increased, to slow down the patient's breathing.

The system can be configured to suit the individual patient's needs and the patient profile. It can store all data relating to the use of the interface, and can connect to a platform to which it can forward the data for further processing and feedback to additional parties.

A first function of the system is to provide breathing guidance with the breathing assist device, and to provide assistance when there is an acute moment of shortness of breath:

During a physical activity COPD patients experience shortness of breath. To regain their normal breathing rhythm they use the breathing assist device. The breathing assist device first measures the breathing rate and compares this with the "normal" or "preferred" setting. Depending on the severity or possible previous data gathered for this particular user, i.e. discrepancy from the "normal" setting, the rate of slowing down the breathing is predicted.

This information is used to set by how much the breathing should be slowed down from one breath to another, e.g. 5% longer, as well as when the guidance is stopped, e.g. five or ten repeated "normal" breathings.

The breathing assist device may indicate too fast breathing to the user by providing an indication such as a low volume but high pitch sound, a red light, or a fast vibration. This signal will change as the breathing is slowed down, either to a lower pitch sound, a yellow-green light or a slower vibration respectively. The signal will disappear once a normal breathing pattern has been regained. Optionally, in addition to this qualitative indication a more quantitative guidance can be implemented on the breathing assist device tool or on the display device.

Figure 2:
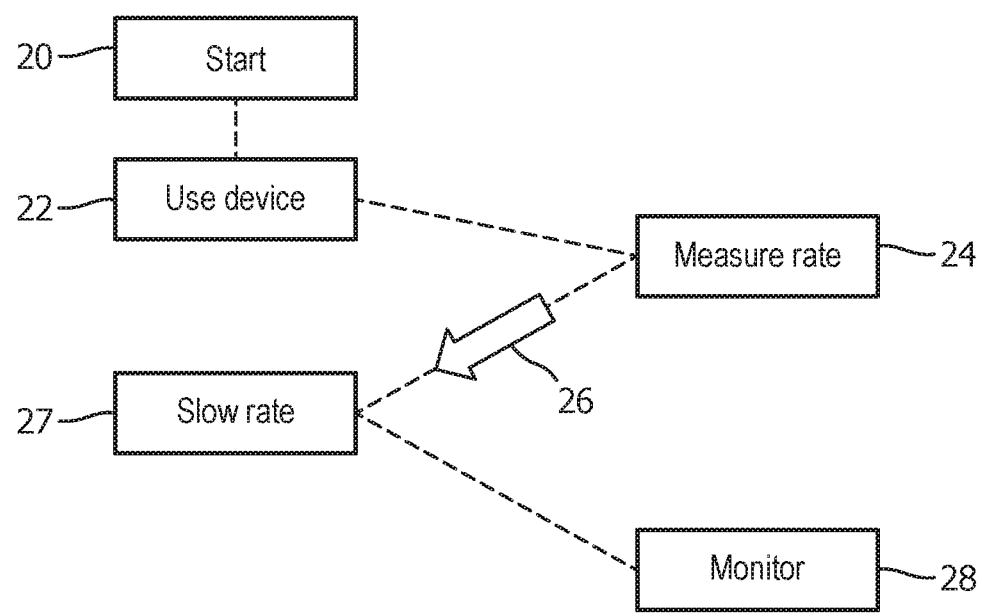
FIG. 2 shows a method of providing breathing assistance.

FIG. 2 shows the sequence of events. The left column of shaded boxes relates to actions or events which relate to the patient and the right column of un-shaded boxes relates to actions or events which relate to the breathing assist device (or the display device).

In step 20, the patient performs physical activity. In step 22 the patient experiences shortness of breath and decides to use the breathing assist device 10. The breathing assist device 10 then in step 24 measures the breathing rate, compares this to a normal rate (for that particular patient) and determines the appropriate slow down rate for the breathing. The required breathing rate is then indicated to the patient as shown by arrow 26. In step 27, the patient slows down their breathing as guided by the breathing assist device 10. The patient's breathing rate is monitored in step 28 to measure the improvement.

In one version, the breathing assist device 10 is also able to deliver positive pressure breathing support. This may for example accompany the guidance to slow down the breathing rate (arrow 26). The positive pressure breathing support may for example increase gradually as in an acute situation additional pressure might be experienced as an additional burden.

By way of example, the breathing rate instruction may initially be decreased and at a certain moment the pressure is increased for an optimized effect.

In addition, data is gathered about the patient performance for feedback to the patient or to a caregiver.

Note that the instructions to the patient may be relayed by the breathing assist device as explained above, or by the display device, or both.

A second function of the system is to provide breathing exercise training.

Figure 3:
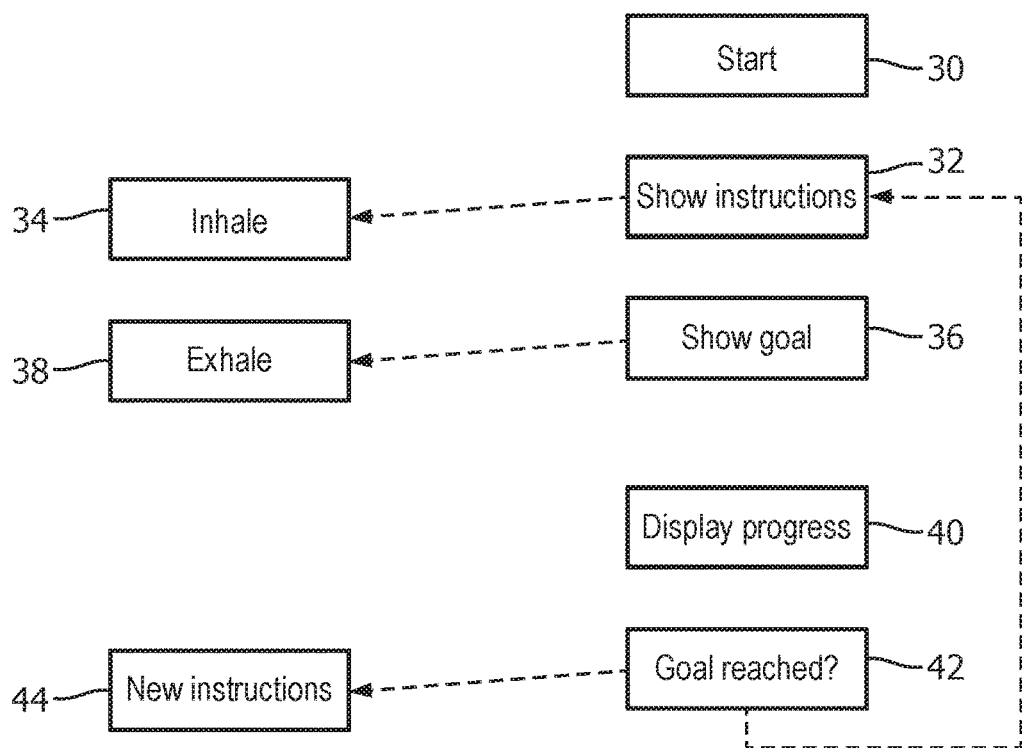
FIG. 3 shows a method of providing breathing exercise training.

FIG. 3 shows the sequence of events. The left column again relates to actions or events which relate to the patient and the right column relates to actions or events which relate to the breathing assist device (or the display device).

The app is started in the display device 12 in step 30 and base parameters are established, such as the background noise, normal breathing rate, etc. The breathing parameters, such as inhalation and exhalation time, flow etc. can be measured using various different sensors such as a flow meter, a microphone possibly attached to the chest, accelerometer attached to the belly, an accelerometer in a smart watch on the wrist, with the patient requested by the smart watch to place the hand on the belly, etc.

The goal of the exercise is to achieve a long exhalation time. This is either a pre-set time depending on the patient's status, e.g. 4-10 sec., or a time established with respect to the base parameters and a pre-set factor, e.g. 2 or 3 times as long. The exercise is repeated several times, e.g. 5-10 times, depending on recommended settings by the doctor (or therapist) or an experience value.

In step 32, the display device indicates to the user the instructions to be followed. The exercise starts with a request provided to the patient to inhale. The patient inhales in step 34. Afterwards a goal is indicated to the user in step 36 that the patient has to reach by exhaling for the pre-set amount of time. During the exhalation shown as step 38, an indicator advances towards the goal to show the patient the progress. This can be implemented in either a rather simple, technical visualization e.g. a line that moves towards the goal line or the second indicator of a watch moving towards a marked time. It can also be visualized in a more fun way, using gaming type approach for example inflating a balloon to a certain size, blowing out candles on a cake with one candle extinguishing per second exhaled or advancing a ball across a goal line, etc.

Step 40 is the display of the advancement towards the goal.

Breathing exercises with the breathing assist device 10 alone can be implemented in a similar way, with the indication on the exhalation duration coming directly from the tool, e.g. by sound, visual or haptic indications.

In step 42, if the goal was reached, a next inhale exhale procedure is started, as shown by the feedback loop to the instruction step 32. If the goal was not reached, a next inhale exhale procedure is started but more time might be allocated for the inhaling. This might be used if the goal has been missed repeatedly. Furthermore, only more time for inhalation is given and the time for exhalation (which was not met previously) may be kept the same. Other events may also be detected such as coughing, in which case a period may be set to allow the patient to recover or the exercise might be interrupted completely.

There may be further instructions to the user in step 44 such as a questionnaire to determine how the patient feels or perceived the exercise. Alternatively, step 44 may relate to another type of breathing exercise. For example if starting with pursed lip breathing, this could be followed by diaphragmatic breathing which is done in a similar way, but recoding different parameters. The exhalation time may be adjusted as this is a more difficult exercise. Depending on the patient's status as well as the disease progression, the user interface can be extended. For example, an extended exercise portfolio may be provided, for example to include diaphragmatic breathing with either an additional device or video analysis to track the belly and possibly the chest and shoulder movement. Different levels of data analysis and feedback may be provided as well as services e.g. for additional information and coaching, as well as direct feedback to a doctor. The system may also implement data collection from additional devices.

The collected sensor data may be evaluated (by a doctor, off-line) in the context of the breathing exercise. The breathing parameters can be significantly different depending on the type of breathing exercise, e.g. for COPD patients diaphragmatic breathing is more difficult to do well and not to start coughing than for pursed lip breathing.

Different settings may be used, for example pursed lip breathing could be performed without a target exhalation duration or an initial, pre-set time to just monitor the overall performance without guidance.

Furthermore, based on the data input, the exercise settings can be adjusted dynamically during one session or from session to session. So, rather than just guiding, a smart solution is possible. For example, if a lot of coughing occurs, the exercise has to be stopped. If the exercise repeatedly cannot be performed well or is performed with ease, then the settings can be adjusted.

Hence, a feedback loop is part of the exercise (game) control unit. For a system without data collection, the breathing exercise settings would have to be set manually, e.g. in discussion with care providers. With collection of sensor data, this can be automated, based on the recorded data which makes it more convenient to use and also gives a lot of test data to the doctor.

In this way, a breathing exercise may be set in a smart way, using analysis of the sensor data (e.g. sound) plus possible other input data, so that medically relevant data can be obtained which are not readily available in any other straight forward way.

As mentioned above, the system can provide positive end pressure support during exhalation and inhalation (BiPAP).

Figure 4:
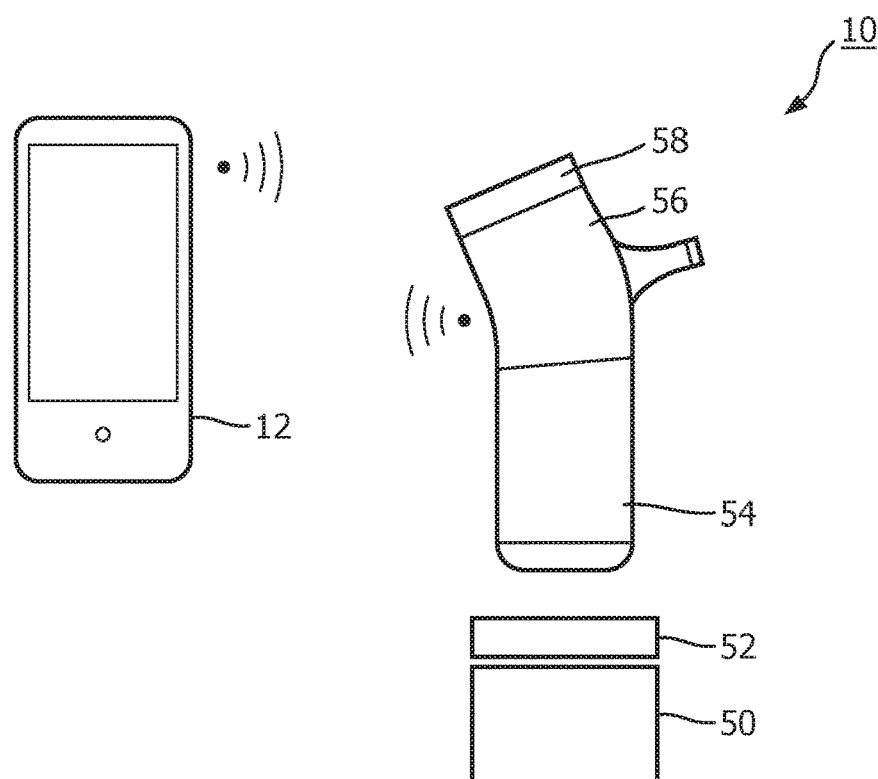
FIG. 4 shows a portable breathing assistance or training system.

FIG. 4 shows the general system.

It comprises a charging station having an air charging unit 50 and an oxygen charging unit 52. They may be stacked one over the other (in either order) or side by side. The breathing assist device 10 comprises a canister 54 for canned air or canned air enriched with oxygen. It may contain almost pure oxygen, then to be mixed with ambient air. The charging station may include electric charging. Air or oxygen enriched air is provided to a patient, for example with a maximum oxygen concentration of about 40%. Pure oxygen is not provided to a patient. If nearly pure oxygen comes from a canister, it is mixed with ambient air.

The main head 56 of the breathing assist device 10 provides sensing of breathing parameters as well as the controlled delivery of the positive pressure to the patient. An optional module 58 is also shown with medication so that the device functions in a similar way to an inhaler. The various parts can be modular so that different combinations of units may be employed. Thus, the modules can be used either via a simple tool without data connection to a remote device, or as a smart tool that also collects data and connects with the app, as shown in FIG. 4. A patient may thus build the modular system starting from the breathing assist device or the display device app, and may also decide to extend or upgrade to a positive pressure BiPAP device with a controller module.

The system includes a pressure control system for providing pressure control during inhalation and exhalation, wherein the pressure control system is controllable to regulate different pressures during inhalation and exhalation. Some examples of suitable pressure control systems are described further below.

The overall system can be extended to connect with additional data sources that deliver data to the app or the platform. These additional devices for example comprise monitoring devices and modalities e.g. heart rate, blood pressure, activity, stress, questionnaires, GPS data (location, direction, velocity and distance), etc.

The device may implement an electronic diary and provide web-based information such as weather conditions and air quality.

Additional devices can for example enable additional breathing exercises such as diaphragmatic breathing as outlined above. Furthermore, additional data can be used to extend the information that can be used for monitoring allowing better insights in the patient's status and hence delivering better feedback and coaching.

The sensing used in the breathing assist device may provide data which can then be analyzed to extract information on the performance (and progression of performance) during and effectiveness of breathing exercises, and adherence to the exercises. The history of usage of the device for training or for intervention is recorded.

Based on this data, intelligence is gathered about the individual patient's situation so that triggers, application settings, coaching options and presented information can be adjusted. Furthermore, long-term changes are identified for disease self-management and status of disease progression.

Certain parts of the information gathered by the system can be provided to third parties including the system provider, relatives and friends (i.e. users of the social community), any informal or formal caregiver, insurance providers and healthcare providers e.g. doctor or nurse.

For example, adherence information may be used by insurance companies or by caregivers. The information exchanged may include not only the sensor data of the breathing assist device itself, but also any other monitoring devices used by the patient.

As mentioned above, the system in some implementations is able to deliver a positive pressure. Currently, PEEP devices provide positive pressure during exhalation, but no guidance for the patient for how long to exhale.

Figure 5:
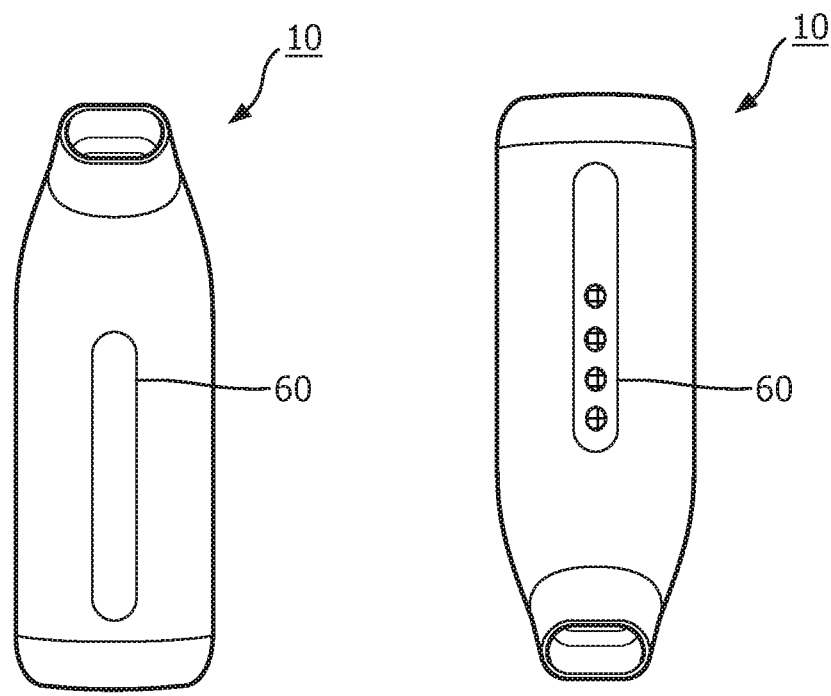
FIG. 5 shows the portable breathing assistance or training device in two different configurations.

In one example, there is provided a visual interface consisting of a series of light sources such as LEDs which can be programmed to light up in a certain color. The breathing assist device 10 is shown in FIG. 5, with a line 60 of LEDs running parallel to an elongate axis of the device, functioning as an output interface to the patient. The breathing assist device is designed to point slightly upward in use, such that the interface 60 comes in the line of sight of the patient and the end of it in focus. The longer the patient exhales, the more and/or further away LEDs light up during exhalation (e.g. in white or yellow). The maximum time is marked with a different LED color (e.g. green), and the patient is incited to try to improve his previous result by exhaling longer, until a pre-set optimum time is reached. A last LED may be used in yet another color (e.g. red or purple) to indicate that the patient is overdoing it.

The display is reset if no exhalation is measured for a certain time such as 3 seconds to provide a reset during inhalation. As in the example above, the data may be collected and sent to an app on the display device 12.

The app running on the display device 12 may have a visual display looking substantially the same as the LED array on the breathing assist device. The display on the app may be fed with the data coming from the breathing assist device, but alternatively also with sound analysis of the exhalation of a patient who is near the app.

In order to determine exhalation, so that the exhalation may be timed, an electrical contact switch is provided on a spring operated valve (as used in Threshold PEP devices), or a pressure sensor in the mouthpiece may be used, in either case to detect exhalation at a sufficiently high pressure. Other sensing approached may be used, for example temperature sensing. A controller measures the signal and controls the programmable strip of LEDs.

As mentioned above, there are various parameters which may be used as an indicator of breathing performance. Breathing exercises implemented as instructions provided on mobile devices are very suitable to relieve anxiety and shortness of breath as explained above. When only using a mobile device (rather than a full sensing breathing assist device as explained above), it is not clear to the user to what extent such exercises are effective and nor do these devices help to monitor the mid and long-term progression of the breathing condition (COPD or Asthma). Such monitoring requires measurement of at least some of the breathing parameters which then typically requires a visit to a clinician. Hence the patients are often not motivated to keep up the exercises as they cannot see the short term effects.

By tracking breathing parameters over time as explained above, progression of the breathing condition is established. This reduces the need to visit the clinician and yields improved accuracy as the amount of instances at which these parameters are measured is increased.

With the exception of flow, the respiratory parameters listed in the introduction above can each be derived from a microphone audio signal when the user is breathing towards the microphone. Thus, breathing exercise applications on mobile devices may be extended by analyzing an audio signal and extracting respiratory parameters. Direct feedback can be given to the patient as well as providing a clinically relevant report on the progression of the breathing condition.

Similarly, a microphone may be used as a parameter sensor as part of the breathing assist device 10.

Figure 6:
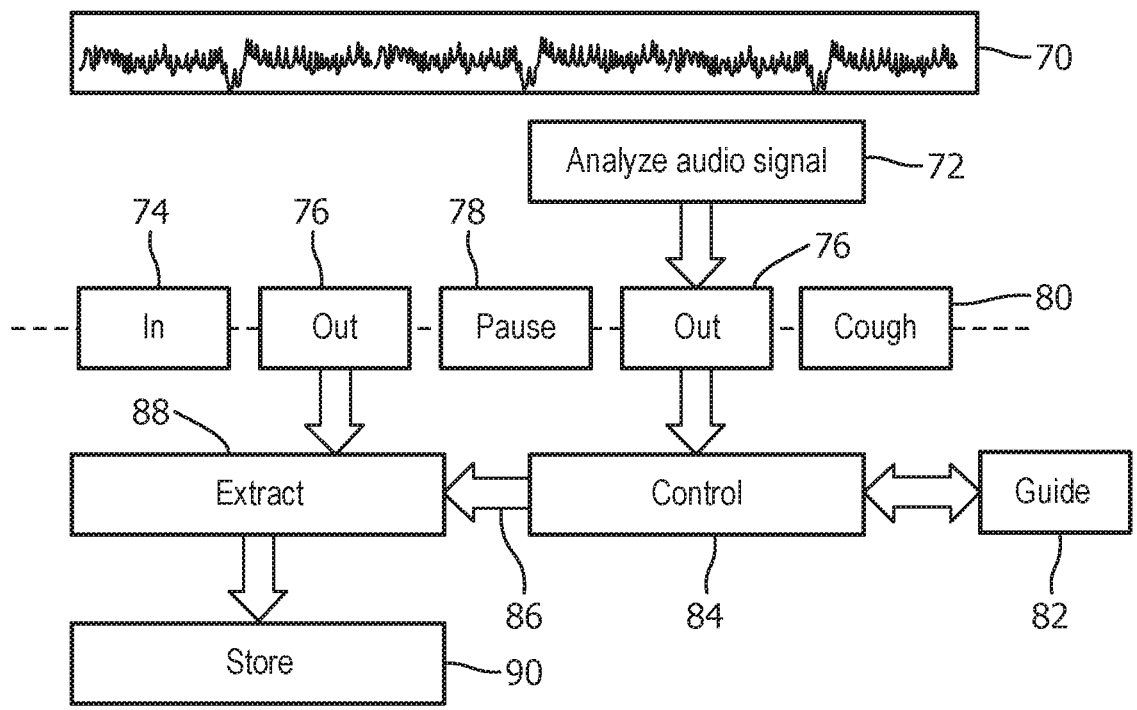
FIG. 6 shows a method of analyzing an audio signal to extract breathing parameters.

FIG. 6 shows a method which makes use of a microphone for providing user feedback.

The breathing exercise application analyses an audio signal 70 in step 72 and converts it to a stream of audio events, such as an in breath 74 an out breath 76, a pause 78 and a cough 80.

These events control the breathing exercise logic 84, guiding the user through the user interface 82 (e.g. the display device 12) and controlling the exercise, for example in a game-based way as explained above.

In parallel, the audio events are analyzed by the respiratory monitor and respiratory parameters are extracted in step 88 and stored in a report in step 90.

The audio signal 70 is the output of a microphone that picks up the user's breathing. Both the breathing exercise routine and the respiratory monitor routine use the audio events for further analysis. The breathing exercise uses the audio signal for direct real time feedback, whereas the respiratory monitor logs the overall performance over the short and long term. Relevant information may for example be the number of coughs per exercise session, the number of exercise repetitions, the number of repetitions executed well, trends during the exercise session and over multiple exercise sessions.

In addition, extra cues 86 about the audio events are sent from the breathing exercise control logic 84 to the respiratory parameter extraction function 88. For example, a breath out event can be due to pursed lip breathing, as instructed by the breathing exercise, and this hint can be used by the respiratory monitor routine to start extracting a respiratory parameter such as the increase in $f_R$ directly after pursed lip breathing.

The extracted respiratory parameters are placed in context in a respiratory report, that is then stored to derive trends or to share with a clinician.

The respiratory report may be enriched with optional sensor data such as accelerometer data to put the respiratory parameters also in the user's lifestyle context. Activity measurements can be correlated to breathing performances for a better estimation of clinically relevant trends, e.g. by distinguishing breathing exercises performed at rest or after physical activity. Additional sensors may also be used as input during the exercise, e.g. to support diaphragmatic breathing exercises by monitoring belly and chest movements.

As discussed above, providing a positive inhalation pressure is one approach to alleviate shortness of breath, and some implementations of the training and monitoring system described above provide this functionality.

This aspect relates to a way to occasionally produce the additional benefits of a positive pressure during inhalation in a low cost, small, lightweight, portable device, while maintaining the most important effect of having a positive exhalation pressure.

Additionally, it is then possible to provide enriching with oxygen, which helps especially with exercise-induced desaturation and the resulting shortness-of-breath. This is particularly common. The combination of positive end expiratory pressure (PEEP) and occasional positive inspiratory pressure (PIP) increases the tidal volume and reduces the work of breathing during an acute episode of dyspnea and reduces the related anxiety.

An episode of shortness of breath usually lasts only a few minutes, and usually patients who experience this have no means of acutely relieving this, even when they know it is coming, leading to panic. The reverse is true too: panic may lead to shortness of breath, thus creating a vicious circle.

A response from inhaling medication is often not quick enough. Training of the lungs, lips and psychological techniques may help using the system as described above, but this requires extensive training, and may be forgotten in case of an acute event. The short duration of such an event leads to the insight that the number of breaths during such an event are quite limited, and that quite a number of them can be supplied with positive pressure, coming from a canister filled with pressurized gas.

As explained with reference to FIG. 4, the gas may be air, oxygen enriched air, or highly enriched oxygen which is then mixed with ambient air.

Figures 7, 8:
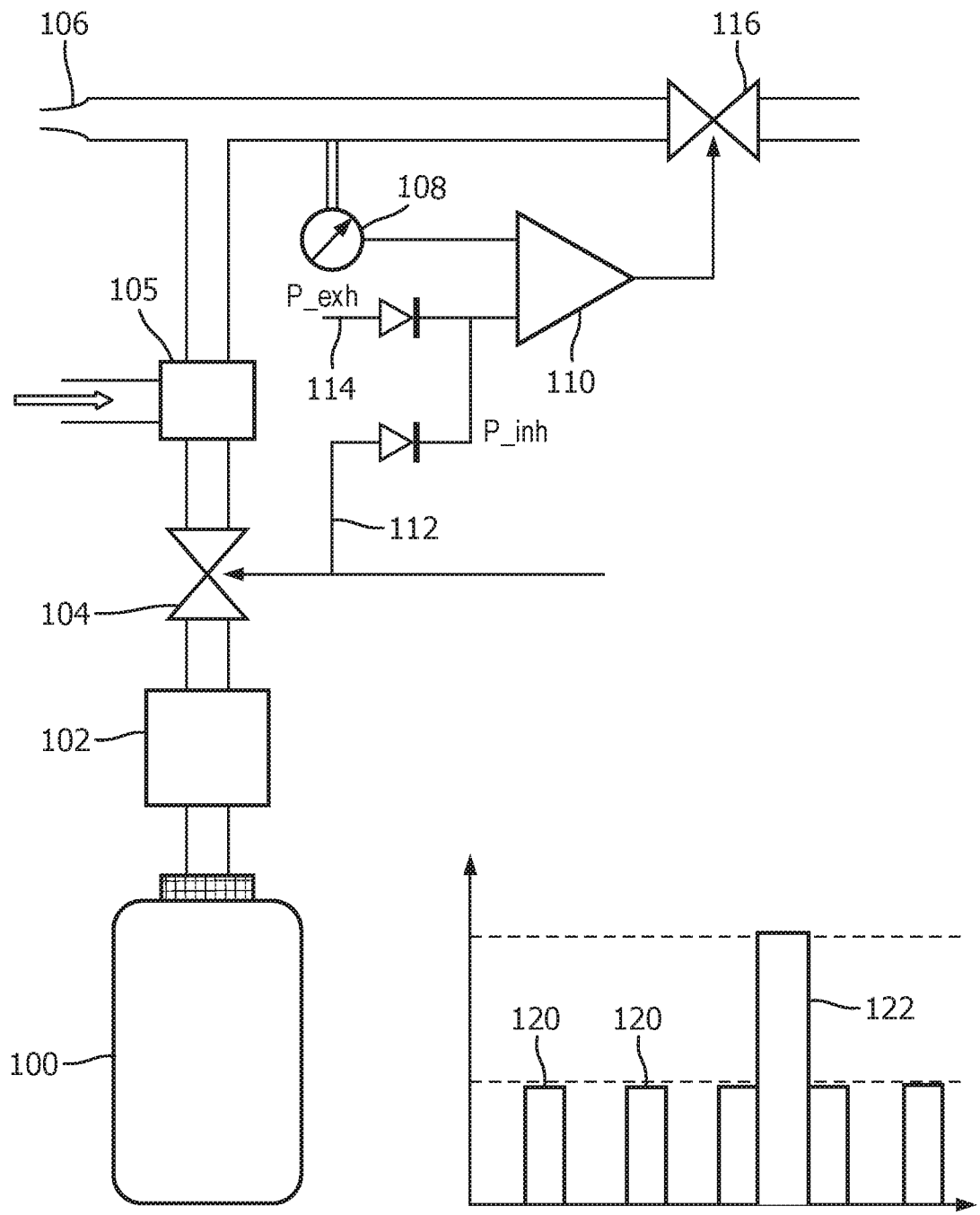
FIG. 7 shows a first example of pressure control system.
FIG. 8 shows a pressure time graph for the device of FIG. 7.

FIG. 7 shows schematically the functional parts of a first example of device for delivering positive air pressure from a small portable canister.

The device comprises a canister 100 in the form of a small pressurized gas bottle. It typically has a volume of 0.2-0.6 L of compressed gas at a maximum pressure of for example 10 atm (1013250 Pa). The output from the gas bottle is connected to a pressure control device 102. In the case of a canister of pressurized air or oxygen enriched air, this comprises a pressure reducer so that the pressure is controllable to a pressure level below the pressurization level. In the case of a canister of enriched oxygen, an injector 105 is provided (either as well as the pressure reducer 102 or instead of it) which is used to mix the oxygen with ambient air.

The outlet from the pressure control device 102 passes through a user controlled valve 104 such as a lever operated valve. The pressure control device for example is used to safely decrease the high canister pressure down to the near ambient atmospheric pressure.

The valve 104 may be of the type used for pressurized oxygen cans, but with the additional feature that upon moving the lever, it also activates a change in the feedback control system described below.

The outlet from the valve 104 passes to the mouthpiece 106 (with injection of ambient air if the injector 105 is needed). The pressure in the tube near the mouthpiece is monitored by a pressure sensor 108, which generates a pressure sensor signal which is provided to a first terminal of a controller, which in this example is shown as a differential amplifier 110. The use of an amplifier circuit provides a simple low cost circuit. The controller may instead be implemented as a processor such as a digital signal processor, which receives the input signals at an analogue to digital converter port. The settings of the inhalation and exhalation pressures p_inh and p_exh may then be adjusted dynamically, even per breath, depending on the analysis of the breathing pattern of the patient during exercise or intervention.

The other terminal of the controller circuit receives one of two possible reference signals. A first higher voltage signal 112 is generated when the lever 104 is open, and it corresponds to an inhale pressure for example of 18 cm $H_2O$ (=1770 Pa). With the lever closed, a second signal 114 is used as the reference, and it corresponds to an exhale pressure for example 8 cm $H_2O$ (=785 Pa). The higher voltage signal overrides the lower voltage signal when the lever is opened as a result of a diode or other circuit arrangement.

The controller generates a control signal to implement feedback control which sets the pressure near the mouthpiece to the reference level, by controlling an electronically operated valve 116 which is coupled between the mouthpiece and the outside.

The valve 116 functions as a restriction through which air is blown. The valve is controllable to different settings, for example opening progressively as the control voltage is increased.

The device is able to provide an occasional positive inspiratory pressure (PIP) during the inspiratory phase, while maintaining the PEEP levels (e.g. 4-30 cm $H_2O$=392-2940 Pa).

The PEEP and PIP pressure settings can be adaptive rather than fixed. They can be manually controlled and regulated by the patient depending upon his requirements and comfortable levels. Alternatively, they may be automatically adapted according to the detected respiratory rate, respiratory phases, respiratory variability etc., if additional sensors are integrated in the device. Moreover, these monitored parameters may be sent wirelessly to an intermediate app or user interface to be shared with the caregivers or clinicians.

The device may for example be separable into two independent modules to provide only exhalation support (PEEP) or the combination of PEEP and PIP.

A device which supports only a PEEP function may for example be used as a training device as an alternative to pursed lip breathing (PLB), when the pressure is set to a minimum level such as 4-5 cm $H_2O$ (392-491 Pa).

The canister may be a small pressurized gas bottle for example less than 1 L, less than 0.6 L and possibly as small as 0.2 L, which can be carried separately and can be connected to the PEEP unit when needed.

The system is able to providing a preferred counter pressure upon exhaling such as 8 cm $H_2O$ (=785 Pa); no or negative pressure upon inhaling, and upon action of the patient, providing a stable higher pressure such as 18 cm $H_2O$ (=1770 Pa), during inhaling.

An injector or mixer may be used not only for enriched oxygen but also for all other types of compressed gas, for example in order to be able to deliver the maximum number of breaths by taking in ambient air.

In use of the system, the patient takes the mouthpiece 106 at the front end of the delivery straw into the mouth when exhaling. Upon reaching the required pressure level (p_exh), the pressure sensor 108 gives a sufficiently high voltage to open the electronic valve 116, to maintain the pressure. For the example of a differential amplifier, by setting the gain level of the amplifier 110, together with the pressure-flow characteristics of the valve, it is possible to have a comfortable effect for a patient that cannot reach the optimum pressure, yet has to be able to exhale.

Upon inhaling, the patient may choose to do either of two actions:

(i) Open the mouth to take a large breath, also having the effect that the pressure in the straw drops to zero, and the electronic valve closes to its minimum opening.

(ii) Every once in a while, the patient may time the pressing of the lever of the user operated valve 104, while keeping the mouthpiece tight with the lips. Air is flowing into the straw, while at the same time the electronic signal is given to maintain the pressure in the straw at a higher level (p_inh).

A typical pressure-time plot is shown in FIG. 8. The small peaks 120 are exhale pressure spikes, and the large peak 122 is when the patient applies the lever while inhaling.

There may be an additional valve in the mouthpiece straw, such that the user also inhales through the straw, and has (slight) under-pressure upon inhaling. This has the additional advantage that the coordination required from the patient is less.

The user operated valve 104 may also be replaced by a machine operated valve, for example which opens every once every predetermined a number of breaths, further diminishing the coordination required from the patient.

The system may make use of other sensors, for example physiological parameters such as respiratory rate, respiratory rate variability, $SpO_2$, $pCO_2$, activity rate etc., may be obtained from any wearable device. These sensor signals can then be fed back to the device to optimize the pressure support or the oxygen content in the respiratory phases.

The system of FIG. 7 has an electronically controlled valve 116. An alternative simpler design can be purely mechanical, driven by the same pressurized gas. The disadvantage of the electronic design is that additional electrical power from a battery is needed so that (more) regular recharging replacement or inspection of the battery is required.

The system above enable at least PEP (Positive Expiratory Pressure), and in more extended exampled also Positive inspiratory Pressure (PIP) during a number of inhalations. The system is intended for small canisters which are bought pre-filled with their compressed gas, being air, enriched air or pure oxygen, depending on the type of patient and/or progression of their disease.

The examples of device above which include a gas canister are generally for use in a crisis situation. Preferably, the user does not have to switch on the device to use it in this mode. The device may thus auto-power-on when it detects patient breathing. One option is to use sensors within the device by leaving them in a low power state, and when a certain threshold is achieved, the device switches into full power mode. Alternatively, a passive actuator may be used to turn on when the airflow through the handset begins. This self-actuation could also extend to a wireless connection to a paired device, to share data or auto-connect at the same time, avoiding additional actions from the patient each time.

Note that the term "portable" when describing the device means that the whole device is portable—rather than there being a portable part and remote fixed part.

As outlined above, two aspects of the system are to provide coaching and to provide prediction of crisis moments. These aspects will now be described in more detail.

In order to be effective, feedback on the effect of an exercise that is being undertaken should be given to the user, and the right type of system output, e.g. coaching or exercise, has to be delivered at the right time. The content and moment of delivery is therefore determined by monitoring various parameters as explained below. The data measured during the use of the system and also additional external data, e.g. from other monitoring devices, may be combined to determine the right type of coaching output as well as to give feedback on the COPD status and progression.

For this purpose, there are various inputs created by the system itself, including the time and date, the local time and duration of use, information about how exercises have been performed (such as how often, how well and if there has been coughing), the breathing rate at the beginning, during and at the end of the exercises, and other breathing related parameters. These may, for example, include flow, overall exhaled volume and attained pressure.

During an exercise, stress level parameters, e.g. worsening of the breathing pattern or external inputs, are measured as well as coughing events to propose a break if the stress level increases above a predefined level or the coughing is too strong. Based on the measurements during use, the performance of the exercise is evaluated: correctness of execution and performance, to gather feedback on the ability to perform the new breathing techniques but also give insights into the patient's status and control of his breathing. If stress levels are increased, this information is stored together with the determined recovery time, i.e. the time needed to slow down the breathing rate/pattern. The ability to slow down the breathing rate with the help of a guided exercise is an indication of how well the patient is in control of his breathing but also the current status and the overall status of the disease. For example, increased coughing during the exercise can highlight an acute or progressive worsening of the disease/symptoms.

There are also possible external data sources, such as SpO2 measurements, indications of use of other systems such as oxygen supplies, inhalers. Physical activity levels, stress and anxiety levels may also be monitored for example with an accelerometer for physical activity and biomedical sensors such as skin conductance for stress and anxiety levels, as well as planned activities (from a diary of the user or from a user questionnaire). Environmental data inputs may also be received such as weather and air quality. There may also be other medical information provided as input for example from a doctor or care provider.

Analysing the internally collected data, together with situational parameters, like location, temperature, air quality, etc., can help identify optimum conditions for physical activity. All this data is fed back into the smart coaching system for learning and adjusting of the exercises (for example different types of exercise) but also to the patient and doctor to better understand the patient's situation, adherence to the program and their disease progression. The data is used not only to provide the right type of advice, exercise or information at the right moment but also to establish a patient history.

The system analyses these inputs and determines the use frequency, circumstances concerning the use, the exercise performance and the effectiveness of the exercise, and the recovery time. All data is stored including data from external sources to enable a complete analysis. The system may then derive exercises for continuous training.

Outputs are provided, for example to suggest an exercise according to the performance level, and to provide feedback on the performance, and changes in performance. Feedback on the disease status and progression is also provided, together with other relevant advice and information. This advice and information for example provides information about long term development of the condition, education on physiology and on COPD, and other general advice about best practices relating to the disease.

The feedback about the disease progression for example may provide long-term breathing rates, the frequency and severity of dyspnea events as well as recovery time from dyspnea events, performance during breathing exercises (coughing events, number of exercises performed, breathing rhythm at beginning and end, etc.), and BODE score.

In this way, internally generated data is combined with externally available data and then used by the system to evaluate and learn about the patient's condition, adherence and performance as well as effectiveness of the breathing exercises. Based on the outcome of this analysis the system delivers the appropriate output at the right time and gives feedback on disease status and progression.

Thus, the data input is used to extract information on the performance of the exercises, the effectiveness of the breathing exercises to achieve breathing rate reduction including recovery time. The frequency and adherence to the exercise program is monitored for example based on the number of planned and actually performed exercises, The user interface is used both for training and for intervention. The data can also be interpreted by using correlation with other lifestyle data and situational data. This enables the system to learn about an individual patient's situation and triggers, leading to different coaching, predictions and advice. Furthermore, long-term changes are identified for disease self-management and status of disease progression.

The analysis of the performance and effectiveness of the breathing exercises is used to reflect the physical status of the patient at that particular moment but also the ability of the patient to overcome a shortness of breath situation, i.e. representing his control of the symptoms. The performance reflects the ability of the patient to correctly perform the exercise for the set number of repetitions in the training mode, i.e. without additional support of the system. The effectiveness of the exercise is measured by the ability to slow down the breathing to the average breathing rate if it was elevated at the beginning of the exercise.

Some examples are now presented to explain the coaching and measuring part of the system, and also to explain how the measured data is analysed and used to determine the right type of output to be provided by the system.

Figure 9:
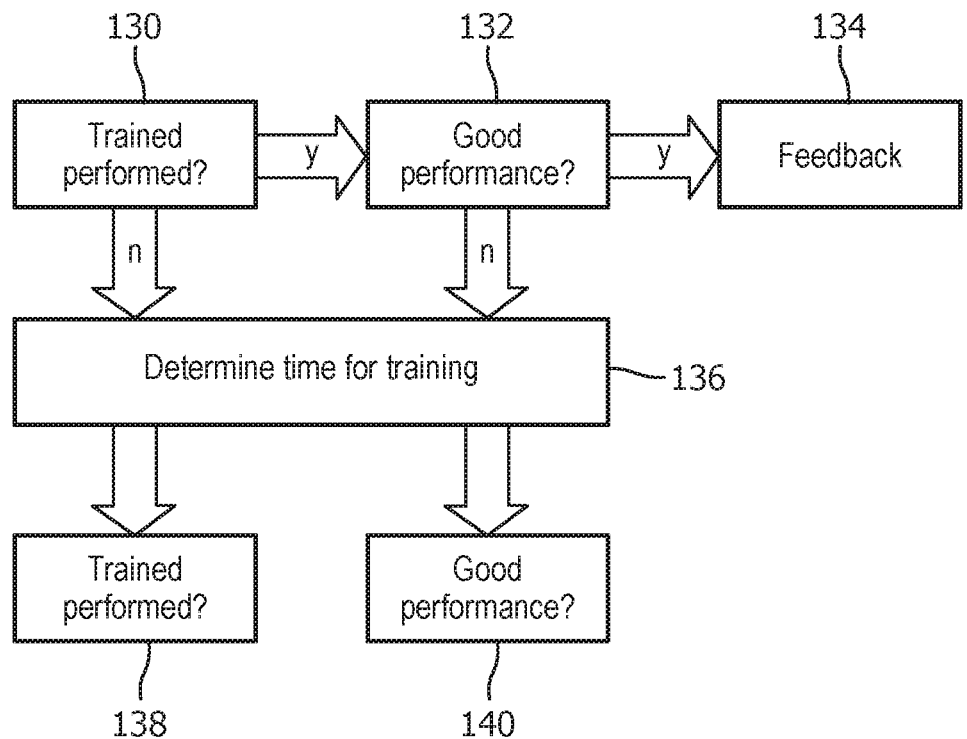
FIG. 9 shows an example of breathing exercise training.

FIG. 9 shows a first example of breathing exercise training.

In step 130, it is determined if breathing exercise training has been performed in a preset previous number of days (e.g. 2 or 3 days). If yes, it is determined in step 132 if the performance was good. If the performance was good, feedback is given in step 134 to motivate continuity and adherence. If the performance was not good, or there has not been a recent training exercise, the method moves to step 136, when a good moment for a new exercise or training is found.

This is for example when the patient has low stress or anxiety, there is good air quality, and there is no other action in the patient's diary. One or more of these factors may be used to determine a suitable time. This ensures that the patient is capable of fully focusing on the exercise and the training is conducted in the most beneficial circumstances.

The exercise or training may be a breathing exercise 138 during which breathing rate, and other parameters (for example measuring stress levels) are monitored. After an exercise, the recovery time is monitored, and a relaxation exercise may be used to support recovery. Feedback on the performance may then also be given.

The exercise can for example be implemented as a serious gaming application to intuitively guide the patient through the exercise (e.g. inflation of a balloon, blowing out candles or blowing away the seeds of a dandelion . . . ). In this way, no extensive explanations are needed as the patient is familiar with the exercise and can perform it well by himself with only minor guidance via the implementation.

The exercise or training may be a training exercise 140 during which the patient is shown the correct posture and guided through an exercise. This may be a more detailed explanation with explicit feedback given during the exercise to make following the exercise easy. At the end, the performance is evaluated and feedback is given on what has improved and what still needs attention.

In both cases, additional information is also provided (at a different moment), to inform and motivate the patient to continue practicing the breathing techniques.

Breathing exercises, such as pursed lip breathing or diaphragmatic breathing as outlined above, help patients to relax, train their respiratory muscles (providing a long-term effect) and help them in adopting new breathing techniques that they can apply to recover from shortness of breath or calm down in other crisis moments. Therefore, it is necessary to learn and practice performing these breathing techniques by regular exercising. The initial breathing rate and the slowing down may be detected, e.g. by sound, breathing flow or pressure analysis.

A patient specific program can be set up, for example to perform breathing exercises at least once per day. The system monitors the frequency of the breathing training and gives advice as outlined below.

The approach of FIG. 9 is generally that if patients do their exercises regularly, the performance is checked. If the performance is good, no additional exercises are proposed, and the system delivers the regular outputs such as general information, and the patient is motivated to continue with the exercises as normal. If the patients do the exercises regularly, but the performance is not good or the execution is not correct, a suitable moment is found to propose a training module. If, however, the last performance of a breathing exercise was too long ago, e.g. more than three days, a suitable moment is identified and the breathing exercise is proposed.

Figure 10:
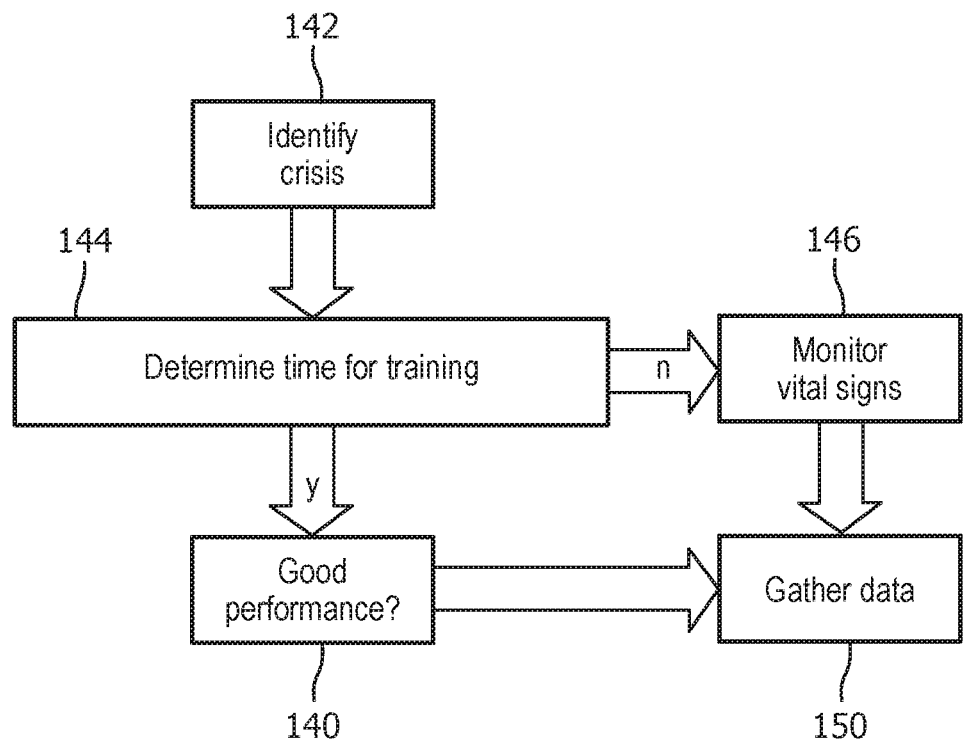
FIG. 10 shows an example of breathing assistance intervention.

FIG. 10 shows a second example, of breathing intervention for example to counteract an acute episode of dyspnea.

In step 142, an acute crisis or at risk moment is identified, during which an intervention or prevention by breathing exercises is needed either to reduce anxiety or provide relieve from dyspnea. A crisis moment may be a time of low activity level and high stress or anxiety.

To identify these acute moments, for example the patient's agenda and several physiological measurements can be used. This can for example be a monitor worn around the wrist that measures COPD patient's physical activity and stress level or a breath monitor to identify moments of shortness of breath based on e.g. stopping activity like walking and using a breathing assist device. Optionally, an additional questionnaire can be used to find out if breathlessness and coughing of the patients increases. The measured data are processed and are made available to patients but can also be made available to the caregiver.

By analysis of the previously gathered data, "at risk" moments can be identified, where the predicted probability of the patient experiencing shortness of breath is high. These indications will typically be done on the basis of the patient history (trends of monitoring data before previous crisis moments), a daily schedule and/or activities planned in the patient's agenda. As a preventative measure, breathing exercises can be proposed to avoid the crisis moment.

In step 144 it is determined if the patient's attention can be caught. This may be issuing a signal from the device or a wrist band of the user. If not, then the vital signs are monitored in step 146 to monitor how the patient gets through the at risk moment without using the device.

If the user responds, step 148 provides a guided exercise to slow down the breathing rate. The breathing exercise can for example comprise pursed lips breathing. After the exercise, the coaching system gives the patient feedback on the performance and long term progress. If in the normal region again the patient is asked to carefully step up and continue the planned actions for the day.

If the patient's monitored data are not better, the patient is asked to repeat the exercise or another relaxation exercise can be proposed. If no improvement can be measured, the monitoring system sends a flag to the caregiver that the patient needs support.

A nurse then contacts the patient and checks the health status and decides with the patient if doctor help is needed.

After the crisis moment is overcome, either with or without execution of the breathing exercises, a questionnaire can further investigate the experience of the patient during the crisis as well as possible triggers, in step 150. The data gathered during the crisis and the potentially performed exercise is stored and analysed to build a better understanding of the patient's triggers for crisis moments to help the prediction of "at risk" moments and to monitor the patient's disease status and his control of the situation.

A longer-term overview of the occurrences of crisis moments and the patient's ability to cope with them can be made available to the patients but also their caregivers for better understanding of the patient's status and investigate possible measures to improve their situation.

Figure 11:
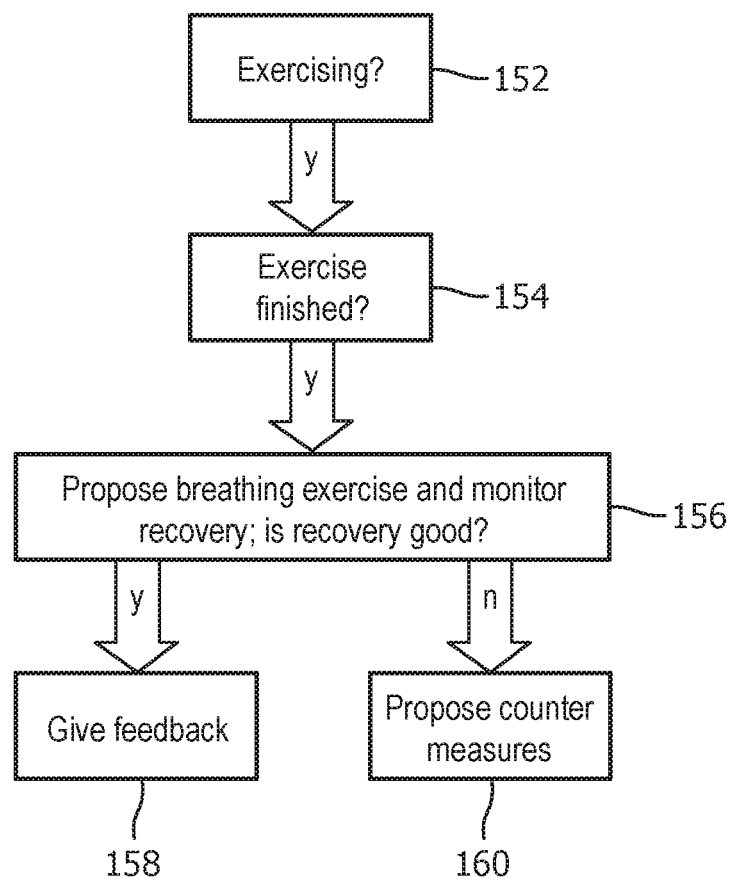
FIG. 11 shows an example of evaluation of recovery after physical exercise.

FIG. 11 shows a third example, of evaluation of recovery after physical exercise.

In step 152 it is determined, based on real time monitoring, that the person is exercising. In step 154 it is determined that the exercise is finished, based on a change in activity level.

In step 156 a breathing exercise is proposed. The recovery time is monitored and parameters are stored such as the initial and final breathing rates, and the time to slow down the breathing rate. In this way, the system detects that an activity has been performed and evaluates the recovery and control of dyspnea via the breathing exercise.

It is determined if the recovery is good. If it is, the exercise is completed and the system gives feedback in step 158.

If the recovery time is longer than usual (compared to previous data), for example indications for shortness of breath are present, counter measures such as relaxation and breathing exercises can be proposed in step 160, as explained above.

If other monitoring devices are connected, other parameters can be monitored to evaluate the effectiveness of the exercise, e.g. heart rate, stress level etc. Monitoring recovery time exercises over an extended time can indicate the stability/worsening of the patient's disease or situation, but also serves as input to adjust the exercise parameters to implement a self-learning system. In order to monitor the status accurately, a breathing exercise such as pursed lip breathing can be used as discussed above.

In addition to using the system for planned exercises, patients may use the system for practicing whenever convenient or to overcome crisis moments. In order to learn more about the general impact on breathing exercises on the experience of shortness of breath for COPD patients, about the individual patient situation, and to give more precise feedback/coaching to the patient, the overall scheduled and un-planned usage of the user interface may be monitored, so that the frequency and use purpose (practicing or intervention in acute moment) of exercises are monitored.

For practicing, the breathing rate will be fairly slow already at the beginning and will only be minimally slowed down but the patient should be able to conduct the exercise well. That means that the effectiveness of the exercise to further slow down the breathing rate will be low, while the performance should be good (or at least average).

In an acute moment, this is most likely the other way round. The breathing rate at the start will be very fast with a large reduction during the exercise. The effectiveness is high, while the performance might be not so good and the exercise might have to be done several times to slow down the breathing. In this way, even by only using the user interface without additional monitoring equipment, training and intervention can be distinguished.

By analyzing a correlation between the occurrences of training sessions and interventions, conclusions can be drawn about how effective the breathing exercise training helps to avoid crisis moments during which the user interface has to be used, and also the effectiveness of overcoming the crisis.

Furthermore, patterns or the change in patterns can be interesting input for third parties, such as doctors or informal care givers.

Table 1 below summarizes changes in use frequency of the user interface, together with possible causes and actions to motivate continuity or change the behaviour or circumstances.

| Practising frequency | Intervention frequency | Conclusion | Actions (by system, caregiver . . . ) |
|---|---|---|---|
| Stable or increased | Decreased | Good control of breathing technique established, intervention with user interface needed less often | Give feedback to patient that clear effect can be seen<br>Ask if experience of shortness of breath is less strong<br>Motivate to continue |
| Stable or increased | Increased | Something changed that requires patient to use interface more often | Investigate change in circumstances by looking at additional data and asking patient (change in living environment, life style, . . . )<br>Test for worsening of COPD condition<br>Give advice to patient for additional measures |
| Decreased | Increased | Change in circumstances or motivation | Investigate change in circumstances (e.g. additional data, ask patient)<br>Give feedback on changes in use frequency<br>Motivate, advice more practicing, change in circumstances |
| Decreased | Decreased | Another factor seems to influence the symptoms of the patient | Give feedback on change in use frequency<br>Investigate what could have positive effect<br>Note as advice to others and motivate patient to keep it up |

When additional data either about other physiological parameters or about the surroundings or general situation are available, further indications can be drawn on the impact of external parameters on the occurrence of a crisis moment.

As explained above, the frequency of breathing exercises being performed is monitored as outlined above. Also, the frequency is monitored and performance of exercises in the training mode, as well as the frequency of acute moments. The effectiveness of the exercise during a crisis moment is determined.

According to the evaluation of these three parameters, the system or a third party can give feedback, motivational messages or suggest other actions, such as changes to the system settings. These actions are summarized in Table 2 below.

| Freq' | Performance | Effectiveness | Feedback to patient | Motivate to | Other actions |
|---|---|---|---|---|---|
| Good | Good | Good | Overall positive | Continue | Possibility to increase: difficulty of exercise level (longer in- & exhale), |

-continued

| Freq' | Performance | Effectiveness | Feedback to patient | Motivate to | Other actions |
|---|---|---|---|---|---|
| | | | | | number of repetitions per session, or frequency of sessions, in agreement with patient. |
| | | Low | Positive on practicing | Continue | Increase number of repetitions per session, or frequency of sessions, whichever patient prefers. |
| | Low | Low | Positive on frequency | Continue | Investigate why performance is low, e.g. is there a need for decreasing difficult level better explanation → extra guided exercises more but shorter training sessions more repetitions? |
| Less than agreed/ advised | Good | Good | Positive on execution | Continue | Investigate why frequency is low Suggest to lower frequency (to a little higher than average use frequency) and increase number of repetitions (keep exercising time per week the same). |
| | | Low | Positive on performance, improvement needed in application during crisis | Practise more | Decrease frequency (slightly) and increase repetitions per session to increase overall time spent exercising per week. |
| | Low | Low | A start is made, but improvement is needed | Practise more | Add teaching sessions (guided exercise) and coaching sessions Lower frequency and add repetitions to increase training time |

Feedback and motivational messages can be sent directly by the user interface. Setting changes and data interpretation as well as investigation of situational changes may be at least verified by a medical professional or addressed in a personal discussion with the patient.

One condition for changing the exercise a patient is to follow is if tasks and exercises or targets are too demanding. A subject or patient can have a bad day due to a bad night sleep, limiting his physical exercise capabilities and limiting his mental capacities. This may mean that requiring too much will result in frustration, leading to a dislike of the coaching which in turn can affect the adherence and thus the system performance.

The overall system in one example is provided with an input which provides quality-of-sleep indicators. This is for example derived from an actigraphy sensor. The data from the actigraphy sensor is then analyzed and interpreted. The analysis typically involves identification of the bed time and an interpretation of the actigraphy data during the night to form a number of quality-of-sleep indicators. Night time is defined the time interval between the moment in which the subject is lying down with the intention to fall asleep and the moment in which the subject stands up from the bed after the night's sleep. The most valuable indicators are the sleep efficiency, the sleep fragmentation, and/or the average sleep bout duration.

The system takes this additional information into account and if the indicators indicate a bad night's sleep, the performance targets (number of exercises, strength and/or duration of the exercise(s)) for the current day are reduced. In this way, the quality of sleep is taken into account in setting targets, for example using a separate sensor for night-time data.

Quality of sleep can be measured by a number of systems such as polysomnography or actigraphy systems. Actigraphy data correlates well with polysomnography, with reliability coefficients ranging from 0.89 to 0.98 for normal sleep. Actigraphy data collection can be done in a relatively unobtrusive way and wearable devices exist for this purpose.

A bad sleep can have a negative influence on the fitness during next day. Indeed, poor sleep has been associated with reduced physical function in older adults.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A device, comprising:
   a housing which defines a mouthpiece;
   a sensor arrangement configured to sense breathing characteristics of a user;
   an input configured to receive external data, wherein the external data relates to one or more of:

environmental conditions in which the device is being used;
activity information in respect of the user;
physiological sensor data about the user which is not related to the breathing characteristics; and
an identification of any medical assistance devices being used by the user;
a controller configured to generate a control signal to implement feedback control and control timing at which output information is provided, based on a prediction of when the output information is most suitable, taking into account the external data; and
an output indicator configured to:
provide the output information relating to breathing instructions or exercises and taking into account the sensed breathing characteristics and the external data, wherein the output information is used to provide feedback to the user and wherein the device includes feedback control of a controlled pressure from a pressure source to provide a positive expiratory end pressure, wherein the feedback control is based at least in part on a position of a user controlled valve, and
display at least one of a time at which exercises or training is to take place and a nature of exercises and corresponding targets to be set for the user.

2. The device as claimed in claim 1, wherein the environmental conditions comprise one or more of:
temperature;
time of day;
weather conditions;
air humidity;
air quality;
location;
noise levels; and
speed of movement.

3. The device as claimed in claim 1, wherein the activity information comprises one or more of:
a current activity level of the user;
a past activity level of the user; and
a future activity schedule of the user.

4. The device as claimed in claim 1, wherein the physiological sensor data represents one or more of:
sleep quality information;
a blood oxygen saturation level;
a heart rate; and
a stress or anxiety level.

5. The device as claimed in claim 1, wherein the sensor arrangement is further configured to measure at least one of a breathing volume, a breathing amplitude, a breathing frequency, or a breathing pattern.

6. The device as claimed in claim 1, wherein the output information is further configured to indicate adherence to breathing exercises, correct breathing performance, or advisory timing information relating to timing at which breathing assistance is to be provided.

7. The device as claimed in claim 6, wherein the output information is to provide an instruction to exhale for a particular time period which takes into account a reference breathing pattern for the user.

8. The device as claimed in claim 1, further comprising:
a connector configured to receive a portable source of pressurized gas, and provide gas to the user at a pressure above atmospheric pressure.

9. A system comprising:
the device as claimed in claim 1; and
a portable display device configured to provide breathing exercise or training instructions to the user.

10. A method of providing breathing training using a portable breathing training device, comprising:
providing, via the portable breathing training device, instructions to a user;
sensing, via the portable breathing training device, breathing characteristics of the user during exercises or training;
receiving, via the portable breathing training device, external data, wherein the external data relates to one or more of:
environmental conditions in which the device is being used;
activity information in respect of the user;
physiological sensor data about the user which is not related to the breathing characteristics; and
an indicator of any medical assistance devices being used by the user;
generating, via the portable breathing training device, a control signal to implement feedback control;
controlling timing at which output information is provided by the portable breathing training device, based on a prediction of when the output information is most suitable, taking into account the external data; and
displaying, via the portable breathing training device, the output information relating to breathing instructions or exercises taking into account the sensed breathing characteristics and the external data, wherein the output information is used to provide feedback to the user, thereby tailoring a breathing exercise or training program, the output information comprising at least one of a time at which exercises or training is to take place and a nature of exercises and associated targets to be set for the user, and
providing, via the portable breathing training device, feedback control of a controlled pressure from a pressure source to provide a positive expiratory end pressure, wherein the feedback control is based at least in part on a position of a user controlled valve.

11. The method as claimed in claim 10, wherein the environmental conditions comprise one or more of:
temperature;
time of day;
weather conditions;
air humidity;
air quality;
location;
noise levels; and
speed of movement, and wherein the activity information comprises one or more of:
a current activity level of the user;
a past activity level of the user; and
a future activity schedule of the user.

12. The method as claimed in claim 10, wherein the physiological sensor data represents one or more of:
sleep quality information;
a blood oxygen saturation level;
a heart rate; and
a stress or anxiety level.

13. The method as claimed in claim 10, wherein the output information is further configured to indicate adherence to breathing exercises, correct breathing performance, or advisory timing information relating to the timing at which breathing assistance is to be provided.

14. The method as claimed in claim 10, further comprising:
  displaying the output information by displaying advancement toward a goal.

15. The method as claimed in claim 10, wherein the device is configured to provide positive end pressure support during both exhalation and inhalation.

16. The method as claimed in claim 10, wherein the device is configured to provide adaptive positive expiratory end pressure (PEEP) and positive inspiratory pressure (PIP) settings.

* * * * *